(12) United States Patent
Theil

(10) Patent No.: US 8,476,061 B1
(45) Date of Patent: Jul. 2, 2013

(54) METHODS FOR ISOLATION, USE AND ANALYSIS OF FERRITIN

(71) Applicant: Slo-Iron, LLC, Walnut Creek, CA (US)

(72) Inventor: Elizabeth C. Theil, Walnut Creek, CA (US)

(73) Assignee: Slo-Iron, LLC, Walnut Creek, CA (US)

( * ) Notice: Subject to any disclaimer, the term of this patent is extended or adjusted under 35 U.S.C. 154(b) by 0 days.

(21) Appl. No.: 13/730,618

(22) Filed: Dec. 28, 2012

Related U.S. Application Data

(60) Provisional application No. 61/581,780, filed on Dec. 30, 2011, provisional application No. 61/581,809, filed on Dec. 30, 2011.

(51) Int. Cl.
*C07K 1/00* (2006.01)

(52) U.S. Cl.
USPC .............. 435/272; 435/22; 435/262; 435/267

(58) Field of Classification Search
None
See application file for complete search history.

(56) References Cited

U.S. PATENT DOCUMENTS

| | | |
|---|---|---|
| 8,071,542 B2 | 12/2011 | Connor et al. |
| 2009/0069217 A1 | 3/2009 | Kato et al. |
| 2010/0093843 A1 | 4/2010 | Schwager et al. |

FOREIGN PATENT DOCUMENTS

| | | |
|---|---|---|
| WO | 2012033812 A1 | 3/2012 |

OTHER PUBLICATIONS

Martin, et al., "Cado-2 Intestinal Epithelial Cells Absorb Soybean Ferritin by μ2 (AP2)-Dependent Endocytosis 1,2" American Society of Nutrition, 2008.
Kimata, et al., "Posttranscriptional Regulation of Ferritin during Nodule Development in Soybean 1", Department of Biochemistry, North Carolina State University, Plant Physiol., vol. 104, 1994.
Beard, et al., "Purified Ferritin and Soybean Meal Can be Sources of Iron for Treating Iron Deficiency in Rats 1, 2", Department of Human Nutrition, Pennsylvania State University, American Institute of Nutrition, 1996.
Lönnerdal, Bo, Soybean ferritin: implications for iron status of vegetarians 1-3', Am J Clin Nutr, American Society for Nutrition, 2009.
Burton, et al., "Evidence for Reutilization of Nodule Iron in Soybean Seed Development", United States Department of Agriculture, Journal of Plant Nutrition, Marcel Dekkar, Inc., 1998.
Davila-Hicks, et al., Iron in ferritin or in salts (ferrous sulfate) is equally bioavailable in nonanemic women 1-3', American Society for Clinical Nutrition, 2004.
Theil, Elizabeth C., "Ferritin", Handbook of Metalloproteins, Children's Hospital Oakland Research Institute, John Wiley & Sons, Ltd, Chichester, 2001.
Ragland, Maria, et al., "Evidence for Conservation of Ferritin Sequences among Plants and Animals and for a Transit Peptide in Soybean*", The Journal of Biological Chemistry, The American Society for Biochemisty and Molecular Biology, Inc. vol. 265, No. 30, Issue of Oct. 25, pp, 18339-18344, 1990.
Murray, et al., "Women with low iron stores absorb iron from soybeans 1-4", Am J Clin Nutr, American Society for Clinical Nutrition, 2003.
Ragland, et al., Ferritin (mRNA, protein) and iron concentrations during soybean nodule developement Plant Molecular Biology, Kluwer Academic Publishers, 1993.
Theil, et al., Absorption of Iron form Ferritin Is Independent of Heme Iron and Ferrous Salts in Women and Rat Intestinal Segments 1-3', The Journal of Nutrition, American Society for Nutrition, 2011.
Atwood, et al., "Comprehensive Supramolecular Chemistry", Suprmolecular Reativity and Transport: Bioinorganic Systems, Elsevier Science Ltd. 1996.
Sczekan et al. "Isolation and Characterization of Ferritin from Soyabeans (Glycine max)*", The Journal of Biological Chemistry, vol. 262, No. 28, Issue of Oct. 5, pp. 13780-13788, 1987.

*Primary Examiner* — Jon P Weber
*Assistant Examiner* — Satyendra Singh
(74) *Attorney, Agent, or Firm* — Laura M. Lloyd; Jeffrey G. Sheldon; Sheldon Mak & Anderson

(57) ABSTRACT

This invention provides methods of isolating ferritin from plant and animal material. The isolated ferritin can be administered to humans or animals in need of iron, and can be used to treat or supplement iron deficiency. The isolated ferritin can be used in industrial applications, such as increasing the iron content in heat-processed food or beverages. The methods of the invention also include quantitation of iron derived from plant or animal ferritin.

15 Claims, 1 Drawing Sheet

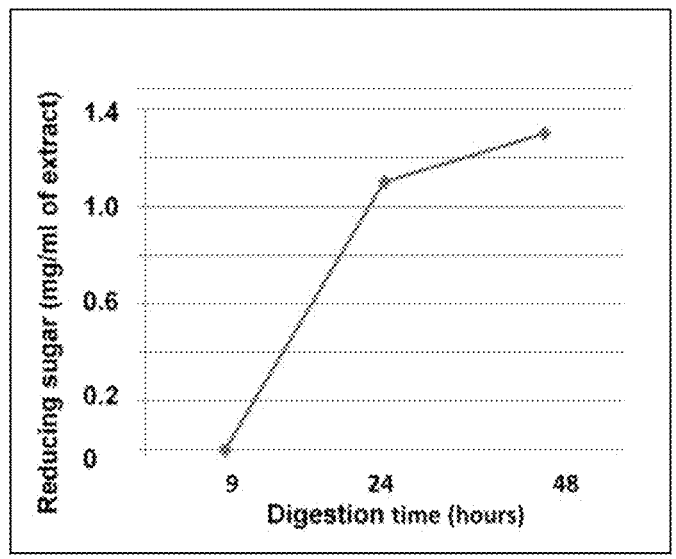

METHODS FOR ISOLATION, USE AND ANALYSIS OF FERRITIN

CROSS-REFERENCE TO RELATED APPLICATION

This application claims priority to and the benefit of U.S. Provisional Application Nos. 61/581,780 and 61/581,809, both filed on Dec. 31, 2011 in the United States Patent and Trademark Office.

BACKGROUND

In humans and other animals, iron is essential for the implementation and maintenance of many vital cellular functions and biosynthetic processes, including oxygen transport, aerobic cellular activity, intracellular electron transport, and integral enzymatic reactions within body tissue. Iron deficiency is the most common nutritional deficiency worldwide, affecting 30 million people in both developed and developing countries. Iron deficiency has many repercussions including diminishing growth and learning in children.

The majority of stored iron in body tissues is contained in ferritin. Ferritin is an intracellular, protein-iron complex, formed from self-assembling subunits. The protein cage can reversibly form iron into a caged biomineral, $Fe_2O_3 \cdot H_2O$, in plants, animals, and bacteria. Iron oxy-biominerals inside the protein nanocages are iron concentrates for protein synthesis, and Fe(II)/oxygen/peroxide traps (Fenton chemistry reactants) for antioxidant protection. The iron contained in ferritin is concentrated 100 billion times above the solubility of ferric ion in a nontoxic, accessible form. Ferritin protein subunits, four α-helix bundles, contain a catalytic center that converts two Fe(II) atoms to an Fe(III)-oxo bridged dimer intermediate in mineralization. The two classes of ferritins are: i) maxi-ferritins, 24-polypeptide, 4-bundle subunit assemblies found in animals, plants, and bacteria; and ii) mini-ferritins (also called Dps proteins), 12-polypeptide, 4-bundle subunit assemblies in archaea and bacteria.

In animals, ferritin is mainly present in tissues, especially in the liver, kidney, spleen and bone marrow erythroid cells where it serves as an iron reserve for the production of hemoglobin. A small fraction of ferritin is in the serum and contributes little to overall iron storage, but is used clinically as a reporter of iron levels in an animal. Ferritins occur in animals as approximately 25 distinct isoforms depending on their proportions of the two primary subtypes of ferritins, H or L. These distinct subtypes differ in their tissue distribution, rates and mechanisms of iron oxidation, core formation and physiological iron turnover.

Ferritin derived from plants and animals can be used as a dietary source for humans and other animals. Ferritin, which survives digestion largely intact, is more efficiently absorbed by the intestine than any other dietary iron source or iron supplement, because of the large amount of iron per ferritin molecule. Ferritin also survives treatment with high heat. The ferritin protein makes ferritin iron a naturally enteric coated, slow release, efficiently absorbed iron source. As such, ferritin can used to supplement iron in animals in need of increased iron in their diet.

Currently, there is a need for methods to isolate plant and animal ferritin from a low-cost, readily available source, which can be administered to a subject in an amount to treat an iron deficiency disorder or prevent iron deficiency. There is also a need for methods to determine the amount of iron derived from animal and plant ferritin.

SUMMARY

The invention describes a method for isolating ferritin from a legume or a legume processing stream by the steps of (a) separation of the legume or the legume processing stream into soluble and insoluble legume fractions; (b) addition of a neutral saline buffer to the insoluble legume fraction to make an insoluble legume solution; (c) clarification of the insoluble legume solution of step (b) into soluble and insoluble legume solution fractions; (d) enzymatic treatment of the clarified soluble legume solution of step (c); (e) fractionation of the enzymatically treated, clarified soluble legume solution of step (d) to remove non-ferritin components; and (f) concentration of isolated ferritin from the fractionated soluble legume solution of step (e).

The invention also describes a method for isolating ferritin from legume or a legume processing stream by the steps of (a) separation of the legume or the legume processing stream into soluble and insoluble legume fractions; (b) addition of a neutral saline buffer to the insoluble legume fraction to make an insoluble legume solution; (c) clarification of the insoluble legume solution of step (b) into soluble and insoluble legume solution fractions; (d) enzymatic treatment of the clarified soluble legume solution of step (c); (e) fractionation of the enzymatically treated, clarified soluble legume solution of step (d) to remove non-ferritin components; and (f) concentration of isolated ferritin from the fractionated soluble legume solution of step (e).

Also described herein is a method to isolate ferritin from plant material by the steps of: (a) separation of the plant material into a soluble and insoluble fraction; (b) removal of non-ferritin components from the soluble fraction of step (a), thereby isolating ferritin; and (c) concentration of the isolated ferritin from step (b). The plant material can be from legumes, such as soybeans.

It is contemplated that the plant material can consist of the entire plant, or it can be a part of a plant, for example one or more of a seed, a bean, a stem, a fruit, a leaf, a root, and a flower. The plant material can be material from the waste stream from processing of legumes.

In one aspect, the step of soluble and insoluble separation can be done by mechanical separation.

It is contemplated that the step of removal of non-ferritin components is done by enzymatic treatment of the soluble fraction. The enzymatically treated non-ferritin components can be removed. The enzyme used to remove the non-ferritin components can be one or more of a glycosidase enzyme.

The isolated ferritin can be concentrated by, for example, drying the soluble fraction, or by ultrafiltration.

Additional steps can be added to the method of isolating ferritin described above, such as fractionation of the soluble fraction either before or after the non-ferritin components are removed. In addition, the soluble fraction can be treated with a solvent such as, for example, an organic solvent.

Also described is a method to isolate ferritin from animal material by the steps of: (a) separation of the animal material into soluble and insoluble fractions; (b) heat-denaturation of the soluble fraction; (d) removal of carbohydrates from the heat-denatured soluble fraction by enzyme digestion; and (c) concentration of the enzymatically treated, heat-denatured soluble fraction. The animal material can be animal tissues such as, for example, the liver, kidney, spleen or bone marrow from an animal.

The step of soluble and insoluble separation can be mechanical separation. The enzyme used in step (d) can be one or more of a glycosidase enzyme. It is contemplated that the heat-denaturation is performed at temperatures below 80° C. Concentration of the isolated ferritin can be accomplished by drying the soluble fraction with low heat, spray drying, or ultrafiltration.

Additional steps can be added to the method of isolating ferritin from animal material, including size fractionation after enzymatic treatment of the soluble fraction. Another step that can be added is treatment of the soluble fraction with a solvent such as, for example, an organic solvent.

The invention is also directed towards the isolated ferritin obtained by the methods described herein.

The invention also describes a method for determining the amount of ferritin iron in a sample wherein the sample has a known weight percentage of a ferritin iron source having the following steps: (a) measuring the total iron in the sample per unit weight of the sample; (b) preparing a soluble extract of a known weight per volume of the sample from step (a) to make a soluble sample extract; (c) determining the total iron per unit weight of the soluble sample extract of the sample; (d) determining the ferritin protein per unit weight in the soluble sample extract, using quantitative immunological analysis; and (e) calculating the amount of ferritin iron in the sample using the amount of the total iron from step (c) divided by the amount of ferritin protein from step (d), multiplied by the amount of total iron in the sample from step (a) multiplied by a correction factor, thereby determining the amount of ferritin iron in the sample. For a sample of legumes, the correction factor is 0.75.

The ferritin iron source used in this method can be material from a plant or an animal. The sample containing ferritin iron can be derived from animal ferritin in the normal tissue or hyperferritinemic serum of a subject.

It is contemplated that the quantitative immunological analysis can be done by any means, for example, quantitative immunoblot, Western blot analysis, and quantitative capillary immunoelectrophoresis.

The invention also describes the use or treatment of a condition caused by iron-deficiency in an organism in need thereof by the use or administration of an effective amount of isolated ferritin obtained by the methods herein.

The organism in need of treatment could be any organism, for example, a plant or an animal such as a mammal, including a human.

The invention also describes a method of increasing the iron content of heat-processed substance by the addition of isolated ferritin obtained from the methods described herein. The isolated ferritin can be added to the substance before the substance is heat-processed. In one embodiment, the heat-processed substance is food. In another embodiment, the heat-processed substance is a beverage.

BRIEF DESCRIPTION OF THE DRAWINGS

These and other features, aspects, and advantages of the present invention will become better understood with regard to the following description, appended claims, and accompanying drawings.

FIG. 1 depicts a graph demonstrating the enzymatic digestion of starch in ferritin extracts over time.

DETAILED DESCRIPTION

Definitions

As used herein, the following terms and variations thereof have the meanings given below, unless a different meaning is clearly intended by the context in which such term is used.

The terms "a," "an," and "the" and similar referents used herein are to be construed to cover both the singular and the plural unless their usage in context indicates otherwise.

The term "buffer" or "buffered solution" refers to a mixture of acid and base which, when present in a solution, reduces or modulates changes in pH that would otherwise occur in the solution when an acid or base is added.

As used herein, the term "comprise" and variations of the term, such as "comprising" and "comprises," are not intended to exclude other additives, components, integers or steps.

A "correction factor" as used herein refers to a number used in calculations of the amount of ferritin iron in a sample. The correction factor is a number that must be multiplied by the minimum percentage of ferritin iron in the original ferritin iron source, because the source of ferritin iron may contain iron in addition to ferritin iron. As such, the correction factor must be used so that an error in calculation does not occur. As an example, in legumes, a minimum of 75% of the iron is ferritin iron, so a correction factor of 0.75 would be used with legume sources of ferritin iron. However, other sources of ferritin iron will have different correction factors.

As used in this specification, the term "ferritin" means the protein with caged iron oxide mineral that confers highly efficient intestinal iron absorption in living organisms and has biological and/or chemical activity and structure the same as, or substantially similar to, a natural, iron-containing ferritin. As such, ferritin includes a naturally occurring ferritin protein with iron mineral or a recombinant, iron mineral-reconstituted ferritin protein, comprising 12 or 24 ferritin subunits, wherein the subunits associate to form a spherical nanocage. Natural ferritins include human ferritin, ferritin from other animals (ferritin derived from horse spleen or bullfrogs, for example), plant ferritin (derived from soybeans, and any other legume or legume process stream for example), microbial ferritins: mycoferritin (derived from fungi), or bacterial ferritin (bacterioferritin) or archaeal ferritin. Ferritin protein includes recombinant ferritin expressed by genetically-transformed microorganisms such as $E.\ coli$, and other bacteria and yeasts. Ferritin expressed by genetically-transformed or recombinant microorganisms can have an amino acid sequence identical or analogous to a natural ferritin. The term ferritin protein can include protein cages consisting of one or both animal isoforms, H and L or plant isoforms (H-1, H-2, etc).

A "ferritin protein subunit" is defined as one of the 12 or 24 polypeptide subunits that make up a ferritin protein. The numbering system used herein for the identification of amino acids within ferritin subunits is based on the original sequence of horse spleen L ferritin (Swiss Protein Database Accession Number P02791). The horse spleen numbering system can be easily converted to a numbering system based on the human H sequence (Swiss Protein Database accession number P02794; the human L sequence accession number is P02792), which has four additional amino acids at the N-terminus. The human H sequence numbering therefore adds 4 to the corresponding amino acid number in horse spleen ferritin. For example, L134 by horse spleen numbering corresponds to L138 by human H sequence numbering. Alignments of ferritin subunit sequences can be found, e.g., in Theil, E. C., in Handbook of Metalloproteins, (Messerschmidt, A. et al., eds.), John Wiley & Sons, Chichester, UK, pp. 771-81, 2001; Waldo, G. S, and Theil, E. C., in Comprehensive Supramolecular Chemistry, Vol. 5, (K. S. Suslick, ed.), Pergamon Press, Oxford, UK, pp. 65-89, 1996.

"Apoferritin" is ferritin in the protein cage, i.e., in the unmineralized state.

A "ferritin pore" is one of the external or internal ferritin cage pores that lead to the eight $Fe^{2+}$ exit/entry ion channels in an assembled ferritin protein cage; the channels and pores are formed by trimers of ferritin subunits. In an intact, 24 subunit ferritin protein cage, there are eight three-fold axes of symmetry, each at a junction of three ferritin subunits. Each ferritin pore and ion channel is formed by these three-way junctions of ferritin subunits. The pores can be visualized in crystals of ferritin proteins by X-ray crystallography and analyzed in solutions by changes in the rate of $Fe^{2+}$ exit.

An "immunoblot" or "immunodetection" is a specific type of biochemical test that measures the presence or concentration of a protein (referred to as the "analyte") in solutions that frequently contain a complex mixture of substances including other proteins. The methods and techniques involved in immunoassays are well known by those in the art.

"Isolation" or "isolation of ferritin" as used herein means separation of ferritin from other components in the plant or animal material, which provides a substantially pure target compound, such as a substantially pure ferritin. Substantially pure ferritin contains ferritin in an amount of from about 50% to about 100%, from about 50% to about 80%, from about 70% to about 85%, from about 65% to about 95% by weight of the total protein in the material processed by the method of the invention.

The terms "individual," "subject" and "patient" are used interchangeably herein, and generally refer to a mammal. The term "mammal" is defined as an individual belonging to the class Mammalia and includes, without limitation, humans, domestic and farm animals, and zoo, sports, and pet animals, such as cows, sheep, dogs, horses, cats and cows.

A "legume" can be one or more soybeans, yellow peas, green peas, lentils, chickpeas (also called garbanzos), peanuts, trefoil, pinto beans, Great Northern beans, navy beans, red beans, black beans, dark or light red kidney beans, fava beans, baby lima beans, pink beans, mayocoba beans, small red beans, black-eyed peas (also called cow peas), cranberry beans, white beans, rice beans, butter beans, and combinations of any of the foregoing. The legume can be any of a variety of species, including, e.g., a *Phaseolus* species (e.g., *Phaseolus vulgaris*), a *Pisum* species (e.g., *Pisum sativum*), a *Lens* species (e.g., *Lens vulgaris*, *Lens culinaris*), a *Cicera* species (e.g., *Cicera arietenum*), a *Vigna* species (e.g., *Vigna unguiculata*), a *Glycine* species (e.g., *Glycine max*), and combinations of any thereof.

The term "nutraceutical formulation" refers to a food or part of a food that offers medical and/or health benefits including prevention or treatment of disease. Nutraceutical products range from isolated nutrients, dietary supplements and diets, to genetically engineered designer foods, functional foods, herbal products and processed foods such as cereal, soup and beverages. The term "functional foods," refers to foods that include "any modified food or food ingredients that may provide a health benefit beyond the traditional nutrients it contains." Nutraceutical formulations of interest include foods for veterinary or human use, including food bars (e.g. cereal bars, breakfast bars, energy bars, nutritional bars); chewing gums; drinks; fortified drinks; drink supplements (e.g., powders to be added to a drink); tablets; lozenges; candies; and the like.

The term "solution" refers to a composition comprising a solvent and a solute, and includes true solutions and suspensions. Examples of solutions include a solid, liquid or gas dissolved in a liquid and particulates or micelles suspended in a liquid.

A "supplement" or "dietary supplement" as used herein is useful for supplementing, replenishing, and increasing the iron supply to humans, animals and plants, and for treating various disorders and conditions. A dietary supplement can be formulated for oral administration. As contemplated in the present invention, a dietary supplement includes ferritin in an amount of from about 10% to about 90% by weight of the total protein in the supplement. For example, subject dietary supplement includes ferritin in an amount of from about 10% to about 15%, from about 15% to about 20%, from about 20% to about 25%, from about 25% to about 30%, from about 30% to about 35%, from about 35% to about 40%, from about 40% to about 45%, from about 45% to about 50%, or from about 55% to about 90% by weight of the total protein in the supplement. For oral preparations, a subject dietary supplement can be formulated with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. A dietary supplement can be administered in one, or more than one, doses per day. A dietary supplement can be administered at various frequencies, e.g., four times daily, three times daily, twice daily, once daily, every other day, three times per week, twice per week, or once per week.

A "therapeutic composition" as used herein means a substance that is intended to have a therapeutic effect such as a pharmaceutical composition, a nutraceutical, a dietary supplement, and other substances. A therapeutic composition may be configured to contain a pharmaceutically acceptable carrier. The therapeutic composition may contain pharmaceutically acceptable excipients, such as vehicles, adjuvants, carriers or diluents. Moreover, pharmaceutically acceptable auxiliary substances, such as pH adjusting and buffering agents, tonicity adjusting agents, stabilizers, and wetting agents.

As used herein, the phrases "therapeutically effective amount" and "prophylactically effective amount" refer to an amount that provides a therapeutic benefit in the treatment, prevention, or management of a disease or an overt symptom of the disease. The therapeutically effective amount may treat a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. The specific amount that is therapeutically effective can be readily determined by ordinary medical practitioner, and may vary depending on factors known in the art, such as, e.g. the type of disease, the patient's history and age, the stage of disease, and the administration of other therapeutic agents.

The terms "treatment" or "treating" as used herein covers any treatment of a condition treatable by iron in a living organism, preferably a primate, and more preferably a human, and includes:

(i) preventing the condition from occurring in a subject which may be predisposed to the condition but has not yet been diagnosed as having it;

(ii) inhibiting the condition, e.g., arresting or slowing its development; or (iii) relieving the condition, e.g., causing regression of the condition.

Stated quantities in the specification and claims are intended to encompass variations of the stated amounts consistent with the practice of the present invention. Such variations are readily determined by one of skill in the art following procedures outlined in specification and typically encode variation on the order of +/−10-20%.

Ferritin Iron

Ferritin is a unique form of dietary iron in that it contains a protein cage with caged iron oxide mineral. In contrast with other iron supplements and dietary iron sources, ferritin's protein coat protects a user's intestine from free radical chemistry caused by iron, which can irritate the intestine. In addition, ferritin iron is released slowly into the blood from the intestine, which also allows for protection of the intestine from free radical chemistry caused by iron.

Plant ferritin contains an average of 1000 iron atoms per protein cage, and animal ferritin contains an average of 1500-2000 iron atoms per protein cage, which allows for more efficient absorption of ferritin iron by the body. In other words, for one transport event in the intestine, the user's body would obtain 1000 times as much iron as it would from non-heme iron salts and chelators.

Ferritin iron is well absorbed by animals. In a rat model, ferritin has been shown to cure iron deficiency. In humans, ferritin iron is absorbed on the order of 20-30%.

Ferritin iron is absorbed by the intestine using a mechanism different from the mechanism of absorption of other iron sources such as non-heme iron supplements or heme iron from meat. Humans have been consuming ferritin iron for millennia in forms such as ferritin-rich legumes, which have been cultivated for 12,000 years. All contemporary cultures include legumes in their traditional and modern diets. In addition, plant ferritin can be eaten by vegans, which is important since many vegan diets are iron deficient and need to be supplemented with iron.

Isolation of Ferritin from Plant Material

Plant material can be used as a starting material to isolate ferritin in a substantially pure form. Ferritin can be isolated from plant material by the steps of: (a) separation of the plant material into a soluble and insoluble fraction, (b) removal of non-ferritin components from the soluble fraction of step (a), thereby isolating ferritin, and (c) concentration of the isolated ferritin from step (b).

This method of ferritin isolation is less labor-intensive and costly than previously described methods. Previous methods of ferritin extraction from plants include the grinding of plant material in liquid nitrogen, followed by the addition of extraction buffer and clarification by filtration and centrifugation. (Ragland, M. et al., J Biol. Chem. 265:18339-44 (1990).) However, such a method is suitable only for research due to the labor-intensive and costly nature of the method.

A typical starting plant material is a legume such as a soybean. In addition to soybeans, yellow peas, green peas, lentils, chickpeas, peanuts, trefoil, pinto beans, Great Northern beans, navy beans, red beans, black beans, dark or light red kidney beans, fava beans, green baby lima beans, pink beans, mayocoba beans, small red beans, black-eyed peas, cranberry beans, white beans, rice beans, butter beans, or a combination thereof can be used as starting plant material.

It is contemplated in the present invention that the plant material used to isolate ferritin can include the whole plant, or any ferritin-rich portion of a plant, e.g., seed, stem, fruit, leaf, root (e.g., nodulating root), flower, stem, etc. In some cases, the source of the ferritin is one or more of a seed, a nodulating root, and a leaf. Where the source of the ferritin is a seed or a bean, the ferritin can be obtained from the whole seed or bean, or a part of a seed or bean, e.g., the hull.

Plant seeds from legumes such as soybeans have a high ferritin content compared to other plant seeds; immature and senescent sections of leaves and as nitrogen-fixing nodules as accumulate ferritin. Soybean seeds have been tested and shown to be a good source of iron for animal and human nutrition (Murray-Kolb et al, Am J Clin Nutr. 77:180-4, 2003; Davila-Hicks et al. Am J Clin Nutr. 80:936-40, 2004; Theil E. C. et al, J Nutr 142: 478-83, 2012; Beard, J. L. et al., J. Nutr. 126:154-60, 1996) and survives human digestion largely intact (Theil E. C. et al., J. Nutr. 142:478-83, 2012). In cell cultures studies, intact ferritin is transported from the apical side of polarized intestinal cell models via receptor-mediated endocytosis (San Martin et al., J Nutr. 138:659-66, 2008). Iron absorbed by the intestine from intact ferritin is processed intracellularly and released from the basolateral side (Theil E. C. et al., J. Nutr. 142:478-83 2012). Purified ferritin and soybean meal are sources of iron for treating iron deficiency in the rat model system. (Beard, J. L et al., J Nutr. 126:154-60 1996).

The starting plant material can also be a processing stream or a waste stream resulting from the processing of soy or other beans. For example, the source of the isolated ferritin can be a waste stream from the production of tofu or soy milk from soybeans. Processing soy for soy milk produces an insoluble by-product of soy, called okara. Either wet or dried okara or other material from legume waste process streams can be used as starting plant material.

The plant material from the waste stream and/or the legumes themselves is treated to isolate the ferritin, followed by concentration of the ferritin. The concentrated ferritin can then be used to treat humans and other animals in need thereof, such as, for example, treatment of an iron deficiency.

The step of separation of the plant material into a soluble and insoluble fraction can be done through any separation technique, such as, for example, mechanical separation.

Non-ferritin components can be removed from the soluble fraction of the separated plant material by any means, such as, for example, enzymatic treatment of the soluble fraction. The enzyme can be one or more of a carbohydrate degrading enzyme(s). In a preferred embodiment, one or more of the enzymes used in the method is a glycosidase enzyme. Alternatively, or in addition, one or more of the enzymes employed in the method can be an amylase, in particular an α-amylase or a β-amylase, an arabinanase, an arabinofuranosidase, a galactanase, an α-galactosidase, a β-galactosidase, a polygalacturonase, a pectin methyl esterase, a rhamnogalacturonase, a rhamnogalacturon acetyl esterase, a pectin lyase, a xylanase, a cellulase, a β-glucosidase, a cellobiohydrolase, a xylosidase, a mannanase, and/or a glucuronisidase. The enzymes are used in a dosage normally employed for degrading carbohydrates.

After enzymatic treatment, the soluble fraction can be dialyzed to remove the low molecular weight, non-ferritin components. Concentration of the isolated ferritin can be achieved by any means, such as, for example, drying the ferritin-containing soluble fraction, or by ultrafiltration.

Additional steps in the method of isolating ferritin can include fractionation of the soluble fraction after the non-ferritin components are removed. In addition, the method of isolating ferritin can include the step of treatment of the starting material or soluble fraction with an inorganic or organic solvent. The solvent treatment can occur before or after the removal of the non-ferritin components from the soluble fraction.

The product of the method of this invention is referred as isolated ferritin, purified ferritin, or substantially purified ferritin. The ferritin isolated by the method of the invention is useful for industrial applications, as described further below.

Extraction of Ferritin from Animal Material

In animals, ferritin is present in high amounts in the liver, kidney, spleen, and bone marrow. The present invention contemplates that ferritin may be derived from the tissues of animals. Iron-containing ferritin derived from animals can be also used by humans and other animals that are in need of increased iron in their diet.

Isolation of ferritin from animal material can be done using the steps of: (a) separation of the animal material into soluble and insoluble fractions; (b) heat-denaturation of the soluble fraction; (c) removal of carbohydrates from the heat-denatured soluble fraction by enzyme digestion; and (d) concentration of the enzymatically treated, heat-denatured soluble fraction, thereby isolating ferritin.

The starting animal material can be animal tissues such as liver, kidney, spleen or bone marrow from an animal.

The separation of soluble and insoluble material can be achieved through any means, such as, for example, mechanical separation.

The step of heat-denaturation can performed at temperatures adequate to denature proteins. It is contemplated that temperatures below 80° C. can be used.

Carbohydrates can be removed from the heat-denatured soluble fraction by any means, such as, for example, enzymatic treatment of the soluble fraction. The enzyme can be one or more of a carbohydrate degrading enzyme(s). In a preferred embodiment, one or more of the enzymes used in the method is a glycosidase enzyme. Alternatively, or in addition, one or more of the enzymes employed in the method can be an amylase, in particular an α-amylase or a β-amylase, an arabinanase, an arabinofuranosidase, a galactanase, an α-galactosidase, a β-galactosidase, a polygalacturonase, a pectin methyl esterase, a rhamnogalacturonase, a rhamnogalacturon acetyl esterase, a pectin lyase, a xylanase, a cellulase, a β-glucosidase, a cellobiohydrolase, a xylosidase, a mannanase, and/or a glucuronisidase. The enzymes are used in a dosage normally employed for degrading carbohydrates. Concentration of the isolated ferritin can be achieved through any means such as, for example, drying with low heat, ultrafiltration, or spray drying.

The addition of other steps in the method to isolate ferritin from animal material is contemplated. For example, the enzymatically treated soluble fraction can be size fractionated to remove the digested carbohydrate material. In addition, the method of isolating ferritin can include the step of treatment of the soluble fraction with an inorganic or organic solvent. The solvent treatment can occur before or after the removal of the non-ferritin components from the soluble fraction.

Industrial Applications

The isolated ferritin obtained by the method of the invention from either plant or animal starting material may have various industrial applications. The isolated ferritin is particularly useful for being added into products for human or animal nutrition, such as food, beverages, nutraceuticals and supplements.

It is contemplated that the isolated ferritin obtained by the methods described herein can be added to a heat-processed substance to increase the iron content of the heat-processed substance. A heat-processed substance can be food or a beverage. The isolated ferritin can be added to the heat-proceesed substance either before or after the substance is heat-processed.

Treatment or Prevention of Iron Deficiency

The methods of the present invention contemplate that a therapeutic or supplementary composition containing the plant or animal ferritin isolated by the methods described above can be delivered to an organism in need of iron by any known means. The organism can be an animal such as a mammal, including a human. Alternatively, the organism can be a plant. In a preferred embodiment, the composition can be delivered orally.

The ferritin containing therapeutic or supplemental compositions of the invention can be administered in dosages sufficient to treat or prevent iron deficiency. A therapeutic or prophylactic amount effective to treat a disorder related to iron deficiency (such as, for example, anemia) by the methods disclosed herein comprises a sufficient amount of the plant or animal derived ferritin agent or therapeutic composition containing plant or animal derived ferritin delivered during the entire course of treatment to ameliorate or reduce the symptoms of the disorder being targeted for treatment. The composition can also contain a pharmaceutically acceptable carrier or excipient. Such carriers or excipients include any pharmaceutical agent that does not itself induce the production of antibodies harmful to the individual receiving the composition, and which may be administered without undue toxicity.

The isolated ferritin agents and therapeutic compositions can be administered by continuous delivery, intermittent delivery, or through a combination of continuous and intermittent delivery. Many factors can influence the dosage and timing required to effectively treat a subject, including, but not limited to, the severity of the disease or disorder, previous treatments, the general health and/or age of the subject, and other diseases present. Moreover, treatment of a subject with a therapeutically effective amount of a composition can include a single treatment or a series of treatments. In addition to their administration individually or as a plurality, the therapeutic compositions of the invention can be administered in combination with other known agents effective in treatment of diseases. In any event, the administering physician can adjust the amount and timing of administration of the therapeutic composition on the basis of results observed using standard measures of efficacy known in the art or described herein.

Quantitation of Ferritin Iron

Rough determination of the ferritin protein and iron concentration in plant extracts has been shown previously using quantitative Western blotting with a rabbit polyclonal anti-soybean ferritin antiserum. (Ragland, M. and Theil, E. C., *Plant Mol. Biol.* 21:555-560, 1993; Kimata, Y. and Theil, E. C., *Plant Physiol.* 104:263-270, 1994; Burton, J. W., et al., *J. Plant Nutr.* 21:913-927, 1998)

The methods of the present invention contemplate an accurate quantitation of iron derived from plant and animal ferritin, either natural or from recombinant apoferritin with reconstituted iron mineral using either classical, quantitative Western blots or automated, quantitative immunoanalysis using capillary electrophoresis in combination with determination of the amount of ferritin iron and quantitation of the total protein in the sample. The iron can be contained in food, dietary supplements, nutriceuticals and the like. Ferritin iron derived from any natural or processed material can be quantitated, including ferritin isolated by the procedures described herein.

In order to determine the amount of ferritin iron in a sample, the sample's weight percentage of a ferritin iron source must be known. The ferritin iron source may be from plant or animal material. The sample can be any type of sample, for example, natural or processed material including samples from food, beverage, plant or animal material. In addition, the amount of ferritin iron in tissue derived from animals or humans can be determined, including the normal tissue or hyperferritinemic serum of a subject.

The steps for determining the amount of ferritin iron in a sample where the sample has a known weight percentage of a ferritin iron source include the steps of: (a) measuring the total iron in the sample per unit weight of the sample; (b) preparing a soluble extract of a known weight per volume of the sample from step (a) to make a soluble sample extract, (c) determining the total iron per unit weight of the soluble sample extract of the sample; (d) determining the ferritin protein per unit weight in the soluble sample extract, using quantitative immunological analysis; and (e) calculating the amount of ferritin iron in the sample using the amount of the total iron from step (c) divided by the amount of ferritin protein from step (d), multiplied by the amount of total iron in the sample from step (a) multiplied by a correction factor, thereby determining the amount of ferritin iron in the sample. The equation is as follows: a(c/d)(correction factor)=e.

The correction factor used in the calculation depends on the source of the ferritin iron in the sample. For example, the correction factor is 0.75 for a sample comprising legumes, which would make the equation above as follows: a(c/d)(0.75)=e.

The quantitative immunological analysis used in step (d) described above can be any type of quantitative immunological analysis such as, for example, a quantitative immunoblot, Western blot analysis, or quantitative capillary immunoelectrophoresis.

It is also contemplated that the components required to determine the amount of ferritin iron in a sample can be provided in a kit.

EXAMPLES

Example 1

Isolation of Ferritin from Plants

In order to isolate ferritin from plants, the starting plant material was separated into soluble and insoluble fractions after adding a neutral, aqueous salt solution buffered at near neutrality. The mixture can be chilled, at room temperature, or heated. In this example, the plant material/salt solution was kept chilled at between 32 and 43 degrees Fahrenheit (0 to 6 degrees Celsius) overnight with slow stifling or agitation. More extreme conditions of temperature, pH and solvent, which do not interfere with the immunoanalysis, might also be used. Next, the plant material/saline extract was filtered, followed by clarification using continuous or static centrifugation at greater than 35,000×g for 20 minutes.

Carbohydrate was partially removed from the soluble fraction obtained from the clarification step. Carbohydrate was removed by a mixture of glycosidase enzymes added either during extraction or after clarification. FIG. 1 shows the removal of a carbohydrate, namely starch or cellulose, in ferritin extracts that were treated with a glycosidase. The graph demonstrates the conversion of carbohydrate in glycosidase-treated ferritin extract to reducing sugars at room temperature over time. In this example, released sugar was measured as the absorbance at 500 nm of the 3,5 dinitrosalicylic acid-sugar complex and analyzed by UV-vis spectrophotometry.

After the carbohydrates were removed enzymatically, the clarified soluble solution was dialysed with size selective membranes in order to remove the digested sugars and enzyme. The fractionated soluble solution was then dried using low heat to concentrate the isolated ferritin.

The resulting preparation containing isolated ferritin is then used as a food or beverage additive, or as a supplement to treat humans and other animals who are iron deficient. To date, concentrations of ferritin of more than 1000-fold have been achieved by this process.

Example 2

Ferritin Isolation from Animals

Ferritin can be isolated from animal material such as, for example, liver, kidney, spleen, bone marrow, or other ferritin-rich source. Isolation of ferritin from animal material can be done using the steps of: (a) separation of the animal material into soluble and insoluble fractions; (b) heat-denaturation of the soluble fraction; (d) removal of carbohydrates from the heat-denatured soluble fraction by enzyme digestion; and (c) concentration of the enzymatically treated, heat-denatured soluble fraction. Iron-containing, isolated ferritin derived from animals can be also used by humans and other animals that are in need of increased iron in their diet.

Example 3

Determination of Total Ferritin Content

The ferritin content can be determined from any substance containing ferritin including a processed substance (i.e., food, supplement, nutriceutical) derived from animal or plant starting material. In this example, the ferritin iron was quantitated in a food sample containing ferritin iron from legumes.

First, the total food iron content was determined. Next, the iron concentration, the percentage amount of the non-legume component and the percentage amount of the legume component of the processed substance was determined. From the resulting numbers, the legume iron content of the total processed substrate was calculated.

The amount of iron per ferritin protein was then determined and for the protein fraction of the extract. To do this, an aqueous extract of the processed substance was prepared using, as an example, 3 milliliters (mls) of extracting material per milligram (mg) of the processed substance. The total iron concentration in the extract is determined. The concentration of specific ferritin protein in the extract is also determined, using a quantitative immunological analysis, e.g. quantitative immunoblot or automated capillary electrophoresis coupled to quantitation of chemiluminesence or fluorescence with an antiserum directed towards whole legume ferritin or to a ferritin peptide, Extract protein concentrations are determined with a standard protein assay, such as the Bradford colorimetric protein analysis, which is based on protein binding of a dye such as Coomassie blue. The dry weight of a sample aliquot is determined. The amount of iron per ferritin protein, the amount of ferritin iron and the amount of total legume protein/ml of extract and /gm of legume starting material is calculated from the combined results of the iron, protein and ferritin-specific immunoanalyses. The maximum and minimum ferritin content of processed food is determined. The amount legume ferritin iron per gram of food is calculated from the grams of legume added per gram of food and the grams of legume ferritin iron/gm of legume added to the processed food. The minimum amount of ferritin per gram of processed food is calculated by multiplying the resulting number by 0.75 to account for the mazimum amounts of nonferritin iron in legumes. If animal ferritin were the source of the ferritin, measurement of heme iron and the corresponding correction to the total iron determination would be made.

In addition to ferritin measured in natural and processed material, the amount of iron-containing ferritin in a tissue, or in serum during hyperferritinemia in animals or humans can be determined by use of a specific antiserum directed towards the ferritin and quantitative immunoanalyses such as Western blotting or automated capillary electrophoresis.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

What is claimed is:

1. A method for the isolation of ferritin from a legume, the method comprising the steps of:
   (a) separation of the legume into soluble and insoluble legume fractions;
   (b) addition of a neutral saline buffer to the insoluble legume fraction to make an insoluble legume solution;
   (c) clarification of the insoluble legume solution of step (b) into soluble and insoluble legume solution fractions;
   (d) enzymatic treatment with one or more glycosidase enzymes of the clarified soluble legume solution of step (c);
   (e) fractionation of the enzymatically treated, clarified soluble legume solution of step (d) to remove non-ferritin components; and
   (f) concentration of isolated ferritin from the fractionated soluble legume solution of step (e).

2. A method to isolate ferritin from plant material comprising the steps of:
   (a) separation of the plant material into a soluble and insoluble fraction;
   (b) enzymatic removal with one or more glycosidase enzymes of non-ferritin components from the soluble fraction of step (a), thereby isolating ferritin; and
   (c) concentration of the isolated ferritin from step (b).

3. The method of claim 2 wherein the plant material comprises legumes.

4. The method of claim 2 wherein the plant material comprises the waste stream from processing of legumes.

5. The method of claim 2 further comprising the step of fractionation of the soluble fraction.

6. The method of claim 2 further comprising the step of treatment of the soluble fraction with a solvent.

7. The method of claim 6 wherein the solvent is an organic solvent.

8. The method of claim 3 wherein the legumes comprise soybeans.

9. The method of claim 2 wherein the plant material comprises the entire plant.

10. The method of claim 2 wherein the plant material comprises one or more of a seed, a bean, a stem, a fruit, a leaf, a root, and a flower.

11. The method of claim 2 wherein the step of soluble and insoluble separation comprises mechanical separation.

12. The method of claim 2 wherein concentration of the isolated ferritin comprises drying the soluble fraction.

13. The method of claim 2 wherein concentration of the isolated ferritin comprises ultrafiltration.

14. The method of claim 1 wherein the legume comprises soybeans.

15. A method for the isolation of ferritin from a legume processing stream, the method comprising the steps of:
   (a) separation of the legume processing stream into soluble and insoluble legume fractions;
   (b) addition of a neutral saline buffer to the insoluble legume fraction to make an insoluble legume solution;
   (c) clarification of the insoluble legume solution of step (b) into soluble and insoluble legume solution fractions;
   (d) enzymatic treatment with one or more glycosidase enzymes of the clarified soluble legume solution of step (c);
   (e) fractionation of the enzymatically treated, clarified soluble legume solution of step (d) to remove non-ferritin components; and
   (f) concentration of isolated ferritin from the fractionated soluble legume solution of step (e).

* * * * *